United States Patent [19]

Baccichetti et al.

[11] 4,312,883

[45] Jan. 26, 1982

[54] FUROCOUMARIN FOR THE PHOTOCHEMOTHERAPY OF PSORIASIS AND RELATED SKIN DISEASES

[75] Inventors: Francarosa Baccichetti; Franco Bordin; Francesco Carlassare; Francesco Dall'Acqua; Adriano Guiotto; Giovanni Pastorini; Giovanni Rodighiero; Paolo Rodighiero; Daniela Vedaldi, all of Padua, Italy

[73] Assignee: Consiglio Nazionale delle Ricerche, Rome, Italy

[21] Appl. No.: 178,292

[22] Filed: Aug. 15, 1980

[30] Foreign Application Priority Data

Aug. 20, 1979 [IT] Italy .............................. 84134 A/79

[51] Int. Cl.$^3$ ..................... A61K 31/37; C07D 493/04
[52] U.S. Cl. ............................. 424/279; 260/343.44; 260/326 D
[58] Field of Search .................... 424/279; 260/343.21

[56] References Cited

PUBLICATIONS

Borolin et al., Studies on the photosensitizing properties of Angelicin, an angular furocoumarin forming only monofunctional adducts with the pyrimidine bases of DNA, The Italian Jour. of Biochemistry, p. 258, 1975.

Primary Examiner—Henry R. Jiles
Assistant Examiner—Jane T. Fan
Attorney, Agent, or Firm—D. Paul Weaver

[57] ABSTRACT

A class of alkyl-substituted angular flurocoumarins, sometimes termed alkylangelicins, useful in the photochemotherapy of psoriasis and in other skin diseases characterized by cellular hyperproliferation or lack of skin pigmentation is disclosed for topical application or systemic administration. Compared with conventional psoralens the described compounds exhibit a lower risk of skin cancer, absence of phototoxicity problems anderithema to the patient so treated. One preferred compound is 5-methylangelicin.

11 Claims, No Drawings

FUROCOUMARIN FOR THE PHOTOCHEMOTHERAPY OF PSORIASIS AND RELATED SKIN DISEASES

BACKGROUND OF THE INVENTION

The present invention relates to a furocoumarin for the photochemotherapy of psoriasis and of other skin diseases sensitive to this treatment, such skin diseases characterized by cellular hyperproliferation or by lack of skin pigmentation.

The furocoumarins, widely diffused in the vegetable world, are well-known. They can be subdivided into two general groups: psoralens, or linear furocoumarins, and angelicins, or angular furocoumarins. A singular characterizing property of linear and angular furocoumarins is represented by their photosensitizing activity, which is evidenced on different biological substrata; such activity, as is known, obtained by the combined action of the furocoumarin and long-wave ultraviolet light (UV-A).

The linear furocumarins (psoralens) are well known for their cutaneous photosensitizing activity. If, for example, the skin of a human or that of a guinea-pig is treated first with linear furocoumarins and successively irradiated with long wave ultraviolet light (UV-A), after a period of about 12–14 hours a cutaneous erythema appears and is followed by a dark pigmentation after some days. This property has already been exploited since 1948 by El Mofty employing a natural psoralen, xantotoxin (8-methoxypsoralen) which is extracted from an Egyptian plant, the *Ammi Majus*, for the treatment of leucodermin or vitiligo. See A. M. El Mofty, "Vitiligo and psoralens", edited by A, M. El Mofty, Pergamon Press, Oxford, 1968. The cure of this skin disease, which is characterized by the presence on the skin of white spots which do not resume their natural pigmentation even if exposed to the sunlight, is effected by treating these spots with a psoralen and successive exposure to UV-A light; this treatment restores the pigmentation.

More recently psoralens have been employed in the photochemotherapy of psoriasis, and of other skin diseases characterized by hyperproliferation of the cutaneous cells, either by oral or topical application. See H. Tronnier et al, "About The Current Status of Methoxsalen UV-A-Therapy in Dermatology", Casteliania 2,267(1974) and J. A. Parrish et al; "Photochemotherapy Of Psoriasis With Oral Methoxsalen and Longwave Ultraviolet Light", N. Eng. J. Med. 291,1207 (1974).

The oral route of administration is simpler than topical application; it permits a better check of the skin-photo-toxicity and an easy control of the skin pigmentation, which gives perfectly homogenous results. Balanced against it, oral administration can produce a possible hepatoxicity; see H. Tronnier et al, Photochemotherapy In Dermatology, in "Photochemotherapy: Basic Technique and Side Effects", Proceedings of the German-Swedish Symposium on Photomedicine in Oberursel (W. Germany) p. 71, Apr. 23–25, 1975, edited by E. G. Jung, Schattauer Verlag, Stuttgart-New York, (1976) and E. Wolff: Report on Round Table, Photochemotherapy (PUVA) of Psoriasis, in "Research on Photobiology", edited by A. Castellani, Proceedings of the VI Int. Congress of Photocology, Rome Aug. 29–Sept. 3, 1976, p. 751, Plenum Press, New York, 1977. Additionally a certain risk of cataract has been reported, in that the psoralens accumulate in the lenses of the eye, which are exposed to the action of the sun light; see S. Lerman et al "A Method For Detecting 8-methoxypsoralen In The Ocular Lens", Science 197, 1287 (1977).

On the other hand the topical application of psoralens appears less simple and more dangerous for other reasons, in that the checking of the phototoxic effect on the skin becomes more difficult. This is because the non-homogenous distribution of the substance causes a less homogenous pigmentation and, moreover, renders a higher risk of skin cancer. See T. B. Fitzpatrick: Discussion, in "Photochemotherapy: Basic Technique and Side Effects", Proceedings of the German-Swedish Symposium on Photomedicine in Oberursel (W. Germany) Apr. 23–25, 1975, p. 120, Supra; G. Rodighiero; "The Problem Of The Carcinogenic Risk By Furocoumarins", Prog.biochem. Pharmacol. 14, 94 (1978); J. H. Epstein, "Risk and Benefits Of The Treatment of Psoriasis", N. Eng. J. Med. 300, 852 (1979); R. S. Stern et al "Risk of Cutaneous Carcinoma In Patients Treated with Oral Methoxsalen Photochemotherapy For Psoriasis", N. Eng. J. Med. 300, 852 (1979).

In spite of these disadvantages, however, photochemotherapy using psoralens in the present state is the treatment of choice and preferable to other less efficacious and more dangerous forms of therapy, among them, for example, the use of only radiation in the form of short wave length ultraviolet (UV-B) light, the use of drugs that are typically regarded as anti-tumor agents or of topical preparations having a coal tar base.

In any case, independently of the type of administration, the basic concept of photochemotherapy consists in exploiting the characteristic properties of the psoralens to inhibit the DNA and RNA synthesis and in cellular reproduction. In the psoralens, nevertheless, these inhibitive properties are closely connected with phototoxic properties which are manifested on the skin by the formation of erythema and successive hyperpigmentation. Up to now it has been very difficult with psoralens to dissociate the desired therapeutic activity from any untoward phototoxic effects.

It is also known that angelicin, that is angular furocoumarin, while it is capable of inhibiting the synthesis of the nucleic acids and arresting cellular division, does not provoke either erythema or hyperpigmentation on the skin. See F. Bordin, et al, "Studies on The Photosensitizing Properties of Angelicin: Contribution of Monofunctional Adducts Furocoumarin-DNA To The Production of The Photosensitized Effects," Ital. J. Biochem, 24, 258 (1975) and M. A. Pathak et al, Bioassay of Natural and Synthetic Furocoumarin (psoralens), J. Inv. Dermatol, 32, 509 (1959). Nevertheless, the photobiological activity of angelicin is very weak, in fact so weak as to be practically not exploitable in therapy, because of its low capacity of photobinding to DNA; see G. Rodighiero et al, Mechanism of Skin Photosensitization By Furocoumarins: Photoreactivity of Various Furocoumarins With Native DNA and with Ribosomal RNA, Biochem. Biophys. Acta 217, 40 (1970).

In the following Table I properties of some of the known linear furocoumarins or psoralens, i.e. 8-methoxypsoralen (8-MOP), 5-methoxypsoralen (5-MOP) and 4,5′,8-trimethylpsoralen (TMP) are compared with the properties of non-linear furocoumarin or angelicin.

TABLE I
Properties of known furocoumarins

| Property | Linear Furocoumarins (8-MOP, 5-MOP, TMP) | Non-linear furocoumarin (Angelicin) |
|---|---|---|
| Photosensitizing activity | known, strong | known, absent |
| Stimulation of melamin pigmentation | strong, well known | absent, not well investigated, unknown |
| Carcinogenicity | known, strong (topical) weak (oral) | unknown, (topical and oral) |
| Mutagenicity | known, strong | known, weak |
| DNA intercalation property | strong and well known | evident and known |
| DNA synthesis inhibiting property | known, strong | known, weak |
| Photobinding capacity to DNA | known, strong | known, weak |
| Monoadduct forming property | known, strong | known, weak |
| Interstrand cross-linking induction in DNA | strong, well known | absent, and known |
| Therapeutic effectiveness in Vitiligo | known, good to excellent | unknown and not investigated |
| Therapeutic effectiveness in psoriasis | known, good to excellent | unknown and not investigated |
| Therapeutic effectiveness in other diseases | known, | unknown |

BRIEF DESCRIPTION OF THE INVENTION

According to the present invention, we have discovered and hereby disclose that photochemotherapy of psoriasis and of other skin diseases can be effected in a form that can be very efficacious and devoid of risks connected with the use of psoralens, employing a furocoumarin which is an angelicin modified by the introduction of one or more alkyl groups onto the furocoumarin structure.

It has been demonstrated that the introduction of alkyl groups, preferably methyl groups, into the angelicin molecule, provides a clear and recognizable increase in the capacity of the intercalation in the duplex DNA and of the photoaddition to the pyrimidine bases of the macromolecule, and therefore a parallel increase of the inhibition capacity of cellular division.

Our invention includes compounds of the general formula:

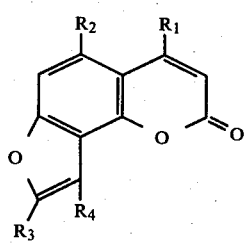

in which $R_1$ and $R_3$, which may be the same or different, are hydrogen or $C_1$-$C_4$ alkyl; $R_2$ is hydrogen, $C_1$-$C_4$ alkyl, methoxy or a group of the general formula:

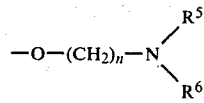

$R_4$ is hydrogen, $C_1$-$C_4$ alkyl, methoxymethyl, hydroxymethyl, acetoxymethyl or a group of the formula:

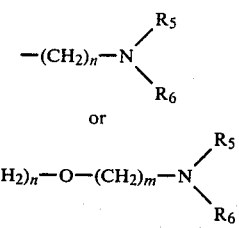

in which $R_5$ and $R_6$, which may be the same or different, are hydrogen or alkyl and both n and m are independently an integer of 1 to 3. The pharmaceutically acceptable salts of such compounds are also included.

In another aspect our invention includes a method of treating psoriasis and other skin diseases susceptible to such treatment in which a compound of the type above is administered to a person suffering therefrom in an effective quantity and thereafter the affected area is subjected to UV-A light irradiation for a period of time. This treatment is continued periodically for a period of weeks until symptoms have been substantially completely or fully alleviated. The compounds are administered in a pharmaceutical preparation, usually for topical application directly to the affected area, or orally, without untoward effects generally associated with previous therapy of this type. Our invention also includes pharmaceutical compositions incorporating one or more of these compounds. Additional information regarding compound synthesis and pharmacological approach are given in detail below.

The alkylangelicins obtained according to the present invention, while presenting therapeutic effects analogous to those of psoralens, are, furthermore, essentially completely or totally devoid of the disadvantages that the psoralens present. In particular they do not provoke any phototoxic effect at skin level, so that the patient is saved from the risk of erythema and, in general, also from successive hyperpigmentation; they facilitate the realization of the topical therapy, since they do not require the very accurate check of the skin-phototoxicity which is absolutely necessary for the psoralens, and this facilitates out-patient therapy; they present only a small mutagenic activity and consequently seem to reduce the possibility of provoking cutaneous tumors. In this connection angelicin and 4,5'-dimethylangelicin have been studied comparatively with some psoralens in various E. coli strains. Only very low mutagenic activity has been observed, that is much lower than that of psoralens, in strains deficient in known repair functions. Mutagenic activity was not detectable in the wild type strains; see S. Venturini et al "Comparative Mutagenicity of Linear and Angular Furocoumarins in E. coli Strains Deficient In Known Repair Functions", Chem.-Biol. Interactions, 30, 203 (1980).

The mechanism of action of furocoumarins (psoralens and angelicins) is known—it is connected with the photo-damage they provoke in DNA. In fact, these substances show a marked affinity towards DNA and act selectively upon it. If, for example, a furocoumarin is added to an aqueous solution of DNA, a complex in the ground state is formed where the planar furocoumarin molecule is intercalated between two base pairs of DNA. When the complex is irradiated with long ultraviolet light (UV-A), the intercalated furocoumarin molecules absorb this light, undergoing excitation and photoreacting with 5,6- double bond of pyrimidine bases of DNA through C-four-cycloaddition reactions. At the level of this photoreaction it is possible to note a profound difference between the linear and the angular furocoumarins.

In fact, two different photoreactive sites, that is 3,4- and 4',5'- double bonds, are present in the furocoumarins (both psoralens and angelicin) and through these sites the C-four-photocycloaddition reations with 5,6- double bond of pyrimidine bases of macromolecule take place.

In particular psoralens, because of their linear structure, can either engage only one of the two photoreactive double bonds forming monofunctional adducts, or both of them realizing two cycloadditions with two pyrimidine bases pertaining to the complementary strands of DNA, forming in such a way an inter-strand cross-linking. See F. Dall'Acqua et al "Inter-strand Cross-Linkages Occurring In The Photoreaction Between Psoralen and DNA", FEBS Letters, 9, 121 (1970). The angelicin, on the other hand, because of its angular structure, can engage, owing to geometrical reasons, only one of the two photoreactive sites, linking to one of the two complementary strands of DAN; see F. Dull'Acqua "Formation of Inter-strand Cross-linkings in The Photoreactions Between Furocoumarins and DNA", Z. Naturforsch., 26b, 561 (1971). In other words, while psoralens in the photoreaction with DNA form both monofunctional and bifunctional adducts, angelicin forms only monofunctional adducts.

In biological terms, the consequences deriving from bifunctional damage are much more serious and dangerous than the consequences deriving from monofunctional damage. It is known in fact that in the living cells DNA—a macromolecule that cannot be replaced by an "ex novo" synthetized copy, in that it can reproduce only by copying itself—represents an essential patrimony that the cell tries to preserve in the best possible way. Since in the habitat it is likely that there is the presence of agents capable of damaging the DNA, such as radiation, chemical agents and the like are present, the cells are endowed with systems capable of "repairing" the possible damage to this macromolecule, which from what has been said above will be seen as an absolute necessity. In the case of photo-damage provoked in the DNA by the furocoumarins, it is known that the cross-links induced by the linear furocoumarins (psoralens) necessarily must be repaired by very complicated processes involving genetic recombination, or by emergency processes, considerably subject to error, such as the so-called S.O.S. repair (see R. S. Cole, "Repair of DNA Containing Interstrand Crosslinks in *Escherichia coli:* Sequential Excision and Recombination", Proc. Nat. Acad. Sci. USA 70, 1064 (1973); A. Belogurov et al "A Mechanism of Inactivation Effect of Photosensitizing 8-methoxypsoralen on Bacteria and Bacteriophages", Mol Biol. (USSR) 12, 886 (1978).

The DNA thus repaired may be modified in the basic sequence and the involved cell can undergo mutations or death; see F. Bordin et al "DNA Repair and Recovery in *Escherichia coli* After Psoralen and Angelicin Photosensitization", Biochem. Biophys. Acta 447, 249 (1976). In the case where the DNA is not faithfully repaired, the involved cell can undergo a neoplastic transformation, and to this phenomenon the carcinogenic activity encountered in certain linear furocoumarins is generally attributed. See D. L. Evans et al "8-methoxypsoralen Induced Alteration of Mammalian Cells", J. Inv. Dermatol. 72, 35 (1979); J. E. Trosko et al "Relationship Between Mutagenesis and Carcinogenesis", Photochem. Photobiol. 28, 157 (1978).

On the other hand, in the case of angelicins (angular furocoumarins), that is, in the case of monoadducts, the lesions can be repaired through simpler and error-free mechanisms, such as the well-known "excision repair"; see R. S. Cole, supra and F. Bordin et al, supra. It follows that the capacity of inducing mutations is much more marked in the case of the psoralens with respect to the angelicins and the necessity of the involvement of error-prone enzymatic systems in the repair of the DNA entails for the psoralens a certain cancerogenic activity as well. This is evidenced in particular in experiments carried out on laboratory animals by repeated topical cutaneous applications and successive irradiation; see D. D. Grube et al "Photosensitizing Effects of 8-methoxypsoralen On The Skin of Hairless Mice, -11-Strain and Spectral Differences for Tumorigenesis", Photochem. Photobiol. 25, 269 (1977). On the contrary, with the angelicins the prospects of a risk of cancerogenesis should be notably reduced given the type of repair of the DNS implicated, and the consequent reduced mutagenic activity; see S. Venturini et al, supra.

In substance, the effects of the angelicins are essentially as follows:

inhibition of the DNA and RNA syntheses and of cellular division, but with lower mortality with respect to the psoralens, as tested in both bacterial and mammalian cell systems;

repair of photodamage with error-free mechanisms with consequent possibility of mutations and of cancerogenesis greatly inferior with respect to psoralens, in which the repair of the photodamage takes place with error-prone systems; according to E. M. Witkin "Ultraviolet Mutagenesis and Inducible DNA Repair in *Escherichia coli*", Bacteriol. Rev. 40, 869 (1976);

absolute lack of phototoxicity on the normal human and guinea pig skin, and thus, unlike the psoralens, elimination of erythema and in general of successive cutaneous hyperpigmentation;

inhibition of the synthesis of epidermal DNA in mice in vivo.

Nevertheless, angelicin has a low photobinding capacity towards DNA and a parallel low photobiological activity which renders this drug unsuitable for therapy. This limitation, according to the present invention, is overcome by modifying the angelicin with the introduction of one or more alkyl groups. In such a way new compounds have been obtained that show a substantial increase of the capacity of intercalation in duplex DNA and a significant increase of photobinding to the pyrimidine bases of the macromolecule, to which corresponds an increased photosensitizing activity. On the basis of their increased photosensitizing activity, and thus on their capacity to inhibit the synthesis of DNA and RNA and to block the cellular division, these compounds appear to be very useful agents for the photochemotherapy of psoriasis and of other skin diseases susceptible to such treatment.

Photochemotherapy with alkylangelicins represents an improvement in respect to photochemotherapy with psoralens; in fact, while producing practically the same therapeutic effect as the psoralens, that is blocking of cellular division at skin level, it does not present the disadvantages of these.

Alkylangelicins and methylpsoralens show a pronounced tendency to dissolve in fats and are therefore only slightly water-soluble. In view of a possible therapeutic improvement water-soluble derivatives or alkylangelicins have also been prepared.

SYNTHESIS OF THE ALKYLANGELICINS

Generally speaking, the preparation of alkylangelicins according to the present invention can be accomplished by different methods, depending on whether or not the alkyl group is present in the furan ring.

The preparation of the alkylangelicins usually starts by condensing resorcin or 5-methylresorcin with malic acid or ethylacetoacetate to obtain the methyl derivatives of 7-hydroxycoumarin. These compounds are then etherified with allylbromide to give the 7-allylethers.

Successively the Claisen transposition of the allylethers furnishes as the main products the 8-allyl derivatives together with a minor amount of the 6-isomers. Particular care must be taken for the purification of 8-allylcoumarins to remove any traces of 6-isomers, since during the successive synthetic steps these compounds lead to the formation of linear furocoumarins, which, according to the present invention, should be absolutely absent because of their skin phototoxicity and capacity to form interstrand cross-linkages.

The invention will be further described with reference to the following examples. Unless otherwise indicated all parts and percentages are by weight.

EXAMPLE 1

A mixture of 5-methylresorcin (25.0 g), malic acid (26.0 g) and conc.$H_2SO_4$ (55 ml) was gently heated with the gaseous development almost ceased. The reaction mixture was then poured with vigorous stirring into a mixture of water and ice (700 ml), and stirred until the gummy mass initially formed was completely dispersed. The precipitate was collected by filtration, washed with water and crystallized twice ($Me_2CO$) producing 5-methyl-7-hydroxycoumarin (I; 15 g; m.p. 256° C.)

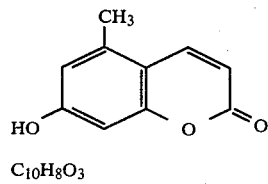

$C_{10}H_8O_3$ free from the isomer 5-hydroxy-7-methylcoumarin (II).

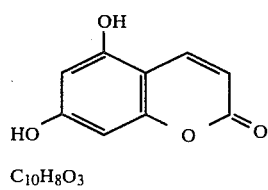

$C_{10}H_8O_3$

EXAMPLE 2

A mixture of 5-methylresorcin (10.0 g), ethylacetoacetate (10 ml) and anhydrous $ZnCl_2$ was heated at 100° C. for 1 hour to produce a semisolid mass to which 5% HCl (10 ml) was added. The mixture was then heated 1 hour longer. The mixture was chilled and filtered and the precipitate washed with $H_2O$ was crystallized from MeOH, to give 4,5-dimethyl-7-hydroxycoumarin, (III; 8.6 g; m.p. 257°–8° C.).

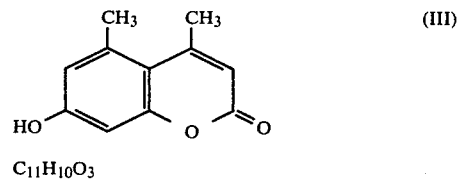

$C_{11}H_{10}O_3$

EXAMPLE 3

A $Me_2CO$ (250 ml) solution of 5-methyl-7-hydroxycoumarin (I; 15.0 g) was reacted with allyl bromide (20 ml) in the presence of $K_2CO_3$ (5.0 g) by refluxing the mixture for 5 hours. After chilling the $K_2CO_3$ is filtered off and washed with fresh $Me_2CO$. The pooled filtrate and acetonic washings were concentrated to dryness and the residue crystallized from cyclohexane giving 5-methyl-7-allyloxycoumarin (IV; 13.8 g; m.p. 83° ).

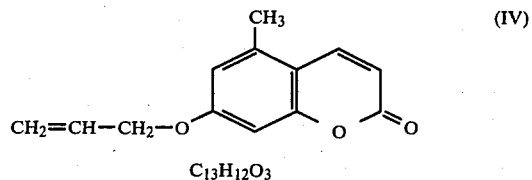

$C_{13}H_{12}O_3$

EXAMPLES 4–6

The following compounds were prepared in the same manner as Examples 1–3 described above: from the 7-hydroxycoumarin (starting material) 7-allyloxycoumarin (V; m.p. 88°–9° C. (from cyclohexane))

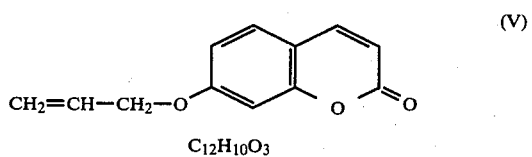

$C_{12}H_{10}O_3$ from 4-methyl-7-hydroxycoumarin 4-methyl-7-allyloxycoumarin (VI; m.p. 107°–8° C. (cyclohexane))

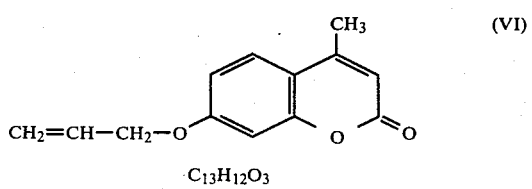

$C_{13}H_{12}O_3$ from 4,5-dimethyl-7-hydroxycoumarin (III) 4,5-dimethyl-7-allyloxycoumarin (VII; m.p. 140° C.; (MeOH))

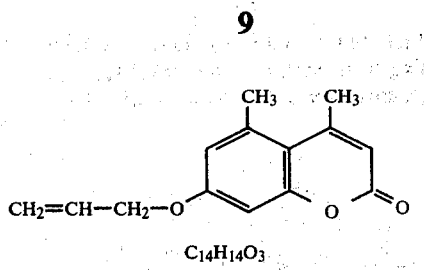

EXAMPLE 7

A solution of 5-methyl-7-allyloxycoumarin (IV; 13.8 g) in diethylaniline (60 ml) was refluxed for 5 hours. After cooling, EtOAc (250 ml) was added and the mixture was washed several times with dil. HCl and then with water; the solvent was evaporated from the dried (Na$_2$SO$_4$) organic phase and the residue by crystallization from EtOAc gave 5-methyl-7-hydroxy-8-allylcoumarin (VIII; 4.5 g; m.p. 177° C.).

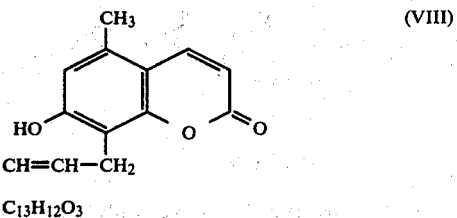

Chromatography on a silica gel column by eluting with CHCl$_3$ of the residue of the mother liquors provided a further crop of the 5-methyl-7-hydroxy-8-allylcoumarin (VIII; 4.9 g), free (by TLC) from the isomer 5-methyl-6-allyl-7-hydroxycoumarin (IX)

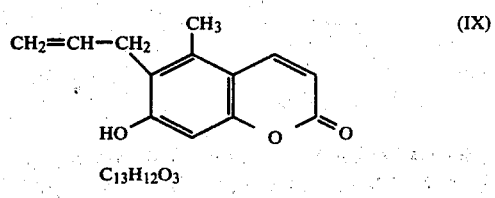

EXAMPLES 8-10

The following compounds were prepared by processing analogous to Example 7: from the 7-allyloxycoumarin (V) 7-hydroxy-8-allylcoumarin (X; m.p. 165° C. (from EtOAc))

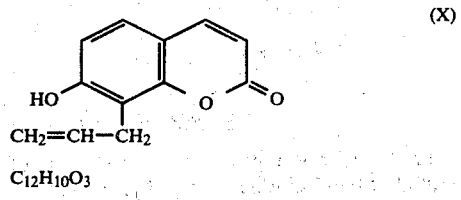

free (by TLC) from the isomer 6-allyl-7-hydroxycoumarin (XI) was obtained

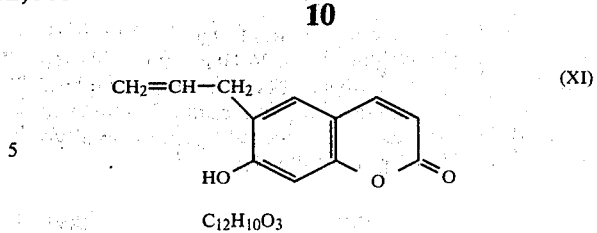

from 4-methyl-7-allyloxycoumarin (VI) 4-methyl-7-hydroxy-8-allylcoumarin (XII; m.p. 195° C. (EtOAc))

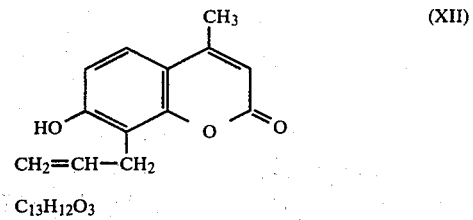

free (TLC) from the isomer 4-methyl-6-allyl-7-hydroxycoumarin (XIII) was obtained

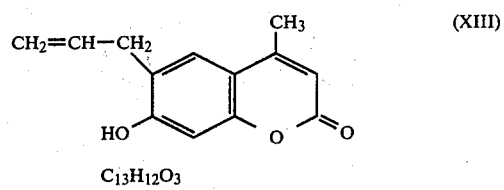

from 4,5-dimethyl-7-allyloxycoumarin (VII) 4,5-dimethyl-7-hydroxy-8-allylcoumarin (XIV; m.p. 178° C. (MeOH))

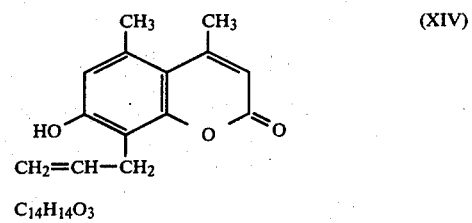

free (TLC) from the isomer 4,5-dimethyl-6-allyl-7-hydroxycoumarin (XV) was obtained

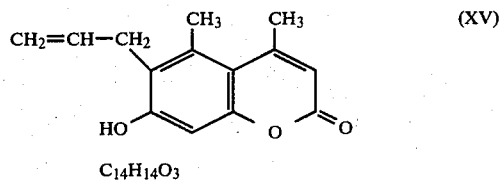

EXAMPLE 11

In order to prepare the alkylangelicin having an alkyl group on the furan ring the 8-allylcoumarins are acetylated and brominated giving the 8-(2',3'-dibromopropyl) derivatives, which are cyclized with ethanolic KOH to give the corresponding 5-methylangelicins.

In this way 5-methyl-7-hydroxy-8-allylcoumarin (VIII; 4.5 g) was refluxed in acetic anhydride (30 ml) containing anhydrous AcONa (1.0 g) for 1 hour. The reaction mixture was diluted with H₂O and refluxed for 10 min., chilled, neutralized with NaHCO and extracted with EtOAc; from the dried (Na₂SO₄) organic phase the solvent was evaporated and the residue crystallized from MeOH giving the 5-methyl-7-acetoxy-8-allyl-coumarin (XVI; 4.3 g; m.p. 113° C.).

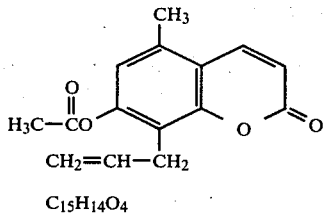

EXAMPLES 12-14

In a manner similar to Example 11 the following compounds were prepared from the indicated starting materials: 7-hydroxy-8-allylcoumarin (X) gave 7-acetoxy-8-allylcoumarin (XVII; m.p. 93°-3.5° C. (from ligroin)

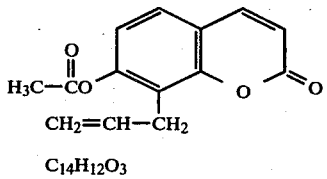

from 4-methyl-7-hydroxy-8-allylcoumarin (XII) the 4-methyl-7-acetoxy-8-allylcoumarin (XVIII; m.p. 101°-2° C. (MeOH)) was produced

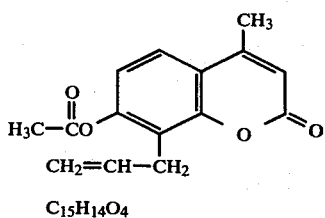

from the 4,5-dimethyl-7-hydroxy-8-allylcoumarin (XIV) the 4,5-dimethyl-7-acetoxy-8-allylcoumarin (XIX; m.p. 166° C. (MeOH)) was produced

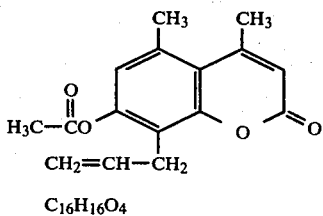

EXAMPLE 15

Into an acetic solution (100 ml) of 5-methyl-7-acetoxy-8-allylcoumarin (XVI; 4.5 g) an acetic solution containing the stoichiometric amount of bromine was added dropwise at room temperature over a period of 30 minutes. After completion of the addition the solution was additionally stirred for 30 min., the solvent was evaporated to dryness and the residue crystallized from MeOH giving the 5-methyl-7-acetoxy-8-(2',3'-dibromopropyl)coumarin (XX; g 5.2; m.p. 139° C.).

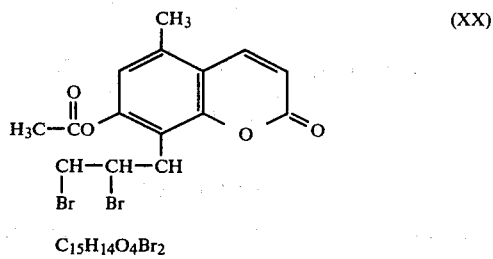

EXAMPLES 16-18

Analogously from 7-acetoxy-8-allylcoumarin (XVII) the 7-acetoxy-8-(2',3'-dibromopropyl)coumarin (XXI; m.p. 123°-3.5° C. (from MeOH)) was obtained;

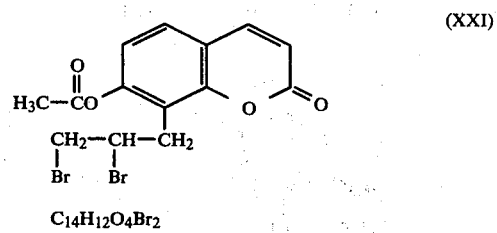

from the 4-methyl-7-acetoxy-8-allylcoumarin (XVIII) 4-methyl-7-acetoxy-8-(2',3'-dibromopropyl)coumarin (XXII; m.p. 156°-7° C. (MeOH)) was produced;

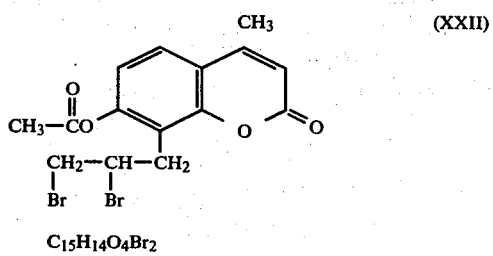

from 4,5-dimethyl-7-acetoxy-8-allylcoumarin (XIX) 4,5-dimethyl-7-acetoxy-8-(2',3'-dibromopropyl)coumarin (XXIII; m.p. 148° C. (MeOH)) was produced.

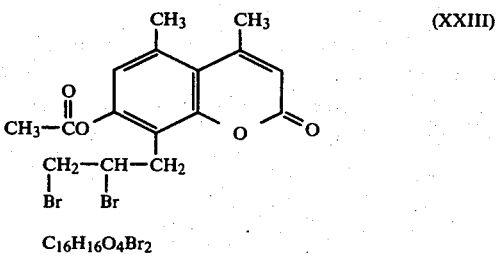

EXAMPLE 19

To an ethanolic solution (100 ml) of 5-methyl-7-acetoxy-8-(2',3'-dibromopropyl)coumarin (XX; 5.2 g) a volume of ethanolic 4% KOH solution equivalent to a molar ratio coumarin/KOH 1:10 was added. The mixture was refluxed for 80 min. in the dark, chilled, diluted twice with a volume of water and acidified with 10% HCl giving a precipitate which was collected by filtration and crystallized from EtOH yielding 5,5'-dimethylangelicin (XXIV) (1.3 g; m.p. 204°-5° C.).

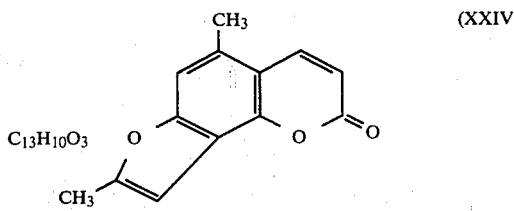

EXAMPLES 20-22

In a manner similar to example 19 7-acetoxy-8-(2',3'-dibromopropyl)coumarin (XXI) 5'methylangelicin (XXV; m.p. 149°-50° C. (from MeOH)) was obtained:

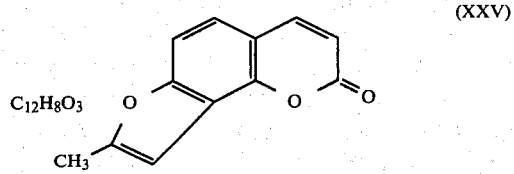

from 4-methyl-7-acetoxy-8-(2',3'-dibromopropyl)-coumarin (XXII) 4,5'-dimethylangelicin (XXVI; m.p. 185° C. (MeOH)) was obtained:

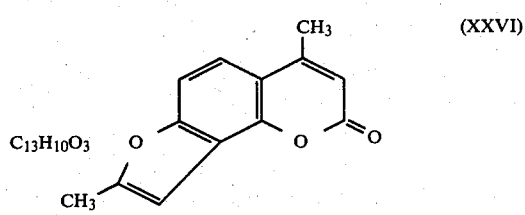

and 4,5-dimethyl-7-acetoxy-8-(2',3'-dibromopropyl)-coumarin (XXIII) 4,5,5'-trimethylangelicin (XXVII; m.p. 203°-4° C. (MeOH)) was obtained:

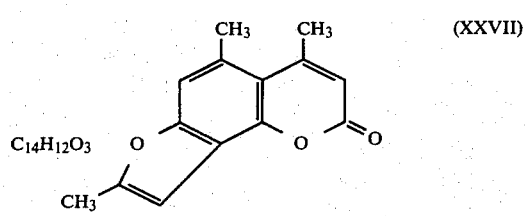

EXAMPLE 23

The following procedure is used to prepare those alkylangelicins without an alkyl group on the furan ring. The 8-allyl derivatives of the coumarins prepared, as previously described, are ozonized to the corresponding 8-coumarinyl-acetaldehydes, which by cyclization with 85% $H_3PO_4$ furnish the desired angelicins.

The following is a specific description of the method: 5-methyl-7-hydroxy-8-allylcoumarin (VIII; 3.0 g) was dissolved in EtOAc (200 ml) and into the solution cooled in an ice bath a stream of ozonized oxygen was bubbled until 1.1 times the stoichiometric amount was added. The solution was then submitted immediately to hydrogenation in the presence of Pd 10% on $CaCO_3$ (0.3 g) and the mixture stirred until rapid absorption of hydrogen ceased. The catalyst was removed by filtration, the solvent evaporated, 85% $H_3PO_4$ (60 ml) added and the mixture heated at 100° C. for 20 min. The mixture was chilled, diluted with two volumes of water and extracted with $CHCl_3$. From the dried ($Na_2SO_4$) organic phase the solvent was evaporated and the residue chromatographed on a silica gel column election with $CHCl_3$ which furnished 5-methylangelicin (XXVIII; 0.63 g; m.p. 191°-2° C. (from MeOH)).

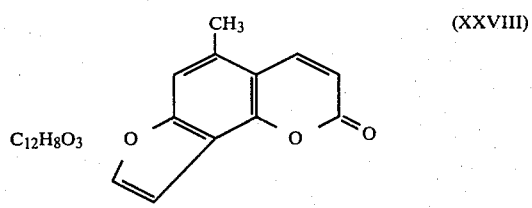

EXAMPLES 24-25

In a manner analogous to example 23, from 4-methyl-7-hydroxy-8-allylcoumarin (XII) 4-methylangelicin (XXIX; m.p. 194°-5° C. (from MeOH)) was obtained:

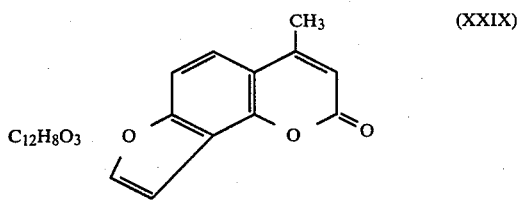

and from 4,5-dimethyl-7-hydroxy-8-allylcoumarin (XIV) the 4,5-dimethylangelicin (XXX; m.p. 211°-2° (MeOH)) was obtained:

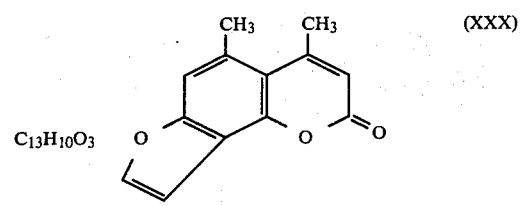

EXAMPLE 26

The 8-coumarinylacetaldehydes (intermediate in the synthesis of those angelicins without an alkyl group on the furan ring) can also be prepared by an alternative method, that is by epoxidation of previously acetylated 8-allylderivatives of the coumarins (see above), by successive hydrolysis of the epoxidate derivatives to diols and then by oxidation of these latter compound with lead tetraacetate.

The following is a specific description serving to further clarify the method; 5-methyl-7-acetoxy-8-allyl-coumarin (XVI; 0.7 g) dissolved in $CHCl_3$ (50 ml) was treated with a stoichiometric amount of a 2% chloroformic solution of perbenzoic acid. The mixture was allowed to stand overnight at room temperature, washed with a $NaHCO_3$ saturated solution and then the solvent was evaporated from the dried ($Na_2SO_4$) organic phase obtaining the 5-methyl-7-acetoxy-8-(2',3'-epoxypropyl)- coumarin (XXXI; 0.58 g; m.p. 126°–7.5° C. (from EtOAc-cyclohexane mixture)).

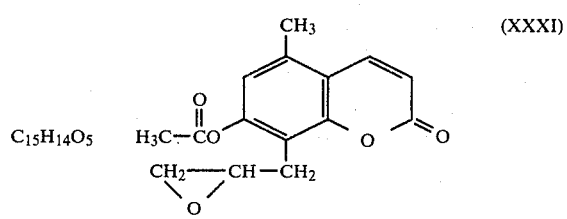

The 5-methyl-7-acetoxy-8-(2',3'-epoxypropyl)coumarin (XXXI; 0.5 g) so produced was suspended in a 1% oxalic acid solution (200 ml) and the suspension refluxed for 10 min. After cooling the reaction mixture was extracted with CHCl$_3$, dried (Na$_2$SO$_4$) and the chloroformic extract was evaporated to dryness. To the residue benzene (20 ml) was added and lead tetraacetate (1.0 g) in small portions while maintaining the temperature at or below 30° C.

After the addition was completed the mixture was stirred for over 1 h the inorganic material was filtered off and washed with benzene. The organic solutions resulting from evaporation of the solvent gave 8-(5-methyl-7-acetoxy) coumarinylacetaldehyde (XXXII; g 0.31)

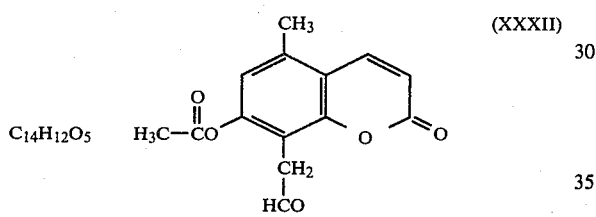

which when treated with 85% H$_3$PO$_4$ as above described gave 5-methylangelicin (XXVIII; 0.1 g). Analogously from the 4-methyl-7-acetoxy-8-allylcoumarin (XVIII) and from the 4,5-dimethyl-7-acetoxy-8-allylcoumarin (XIX) the corresponding 4-methylangelicin (XXIX) and 4,5-dimethylangelicin (XXX), respectively, are obtained.

EXAMPLE 27

Angelicins having a methoxy group in the 5-position are prepared starting from 5-methoxy-7-hydroxycoumarin or from the 4-methyl analog as shown below. According to the following illustrative description.

Floroglucin (20.0 g) was condensed with ethylacetoacetate (40 ml) in ethanolic solution by adding conc. HCl (10 ml) and refluxing the mixture for 2 h. After cooling an abundant crop of a white solid was obtained, which was collected by filtration and crystallized from MeOH giving the 4-methyl-5,7-dihydroxycoumarin (XXXIII: 24.0 g), m.p. 300°–2° C.

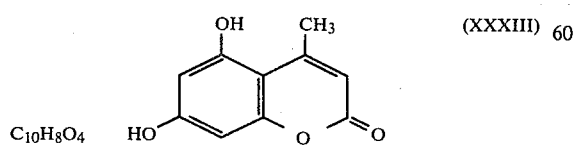

A mixture of 4-methyl-5,7-dihydroxycoumarin (XXXIII; 3.0 g) acetic anhydride (20 ml) and dry Na acetate (5.0 g) was refluxed for 1 h. Water was added (300 ml) and the mixture refluxed for over 1 h. A precipitate was obtained by cooling, then collected and crystallized from MeOH, to give 4-methyl-5,7-diacetoxycoumarin (XXXIV; g 24.8; m.p. 148°–9° C.).

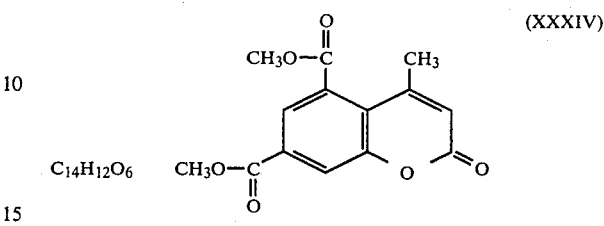

The 4-methyl-5,7-diacetoxycoumarin (XXXIV) was dissolved in dimethoxyethane (80 ml) and a solution of dry K$_2$CO$_3$ (6.6 g) and methyl iodide (3 ml) was added. The mixture was refluxed for 6 h, the solvent was evaporated and the residue, after addition of water:methanol (50:50; 80 ml), was heated to reflux 20 min. By evaporation of the MeOH under reduced pressure and by cooling a precipitate was formed, which by crystallization of first from MeOH and then from Me$_2$CO gave 4-methyl-5-methoxy-7-hydroxycoumarin (XXXV; 1.52 g; m.p. 261°–3° C.).

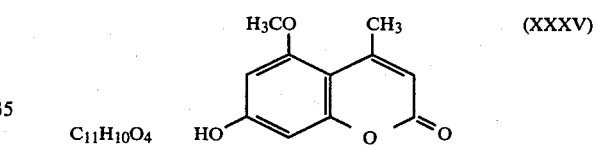

Six grams of 4-methyl-5-methoxy-7-hydroxycoumarin (XXXV) was reacted under reflux for 4 h in acetonic solution (120 ml) with allylbromide (12 ml) in the presence of K$_2$CO$_3$ (4 g). After cooling the solid was filtered off, washing with abundant fresh Me$_2$CO and from the pooled filtrate and washings the solvent was removed by evaporation. The residue was crystallized twice from MeOH giving the 4-methyl-5-methoxy-7-allyloxycoumarin (XXXVI; 4.40 g; m.p. 141° C.).

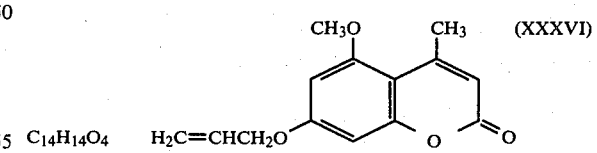

A solution of 4-methyl-5-methoxy-7-allyloxycoumarin (XXXVI; 4.0 g) in diethylaniline (80 ml) was refluxed for 3 h. After cooling, n-hexane (400 ml) was added and the precipitate was collected, washed several times with n-hexane and crystallized twice from EtOAc to give 4-methyl-5-methoxy-7-hydroxy-8-allylcoumarin (XXXVII: 2.8 g; m.p. 198° C.) free from its isomer, the 4-methyl-5-methoxy-6-allyl-7-hydroxycoumarin (which during the successive steps can lead to the formation of a linear furocoumarin).

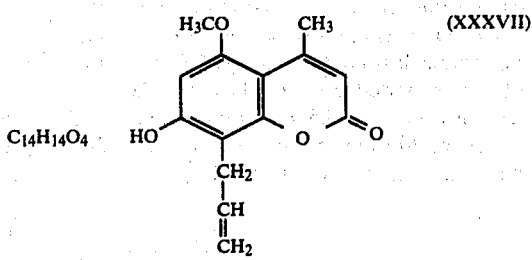

The 4-methyl-5-methoxy-7-hydroxy-8-allylcoumarin (XXXVII; 3.0 g) produced above was reacted with acetic anhydride in the presence of NA acetate (4.0 g) by refluxing the mixture for 1 h. Water was added and the mixture refluxed an additional 20 min. Additional water (200 ml) was added, cooled and the precipitate formed is collected and crystallized from MeOH giving the 4-methyl-5-methoxy-7-acetoxy-8-allylcoumarin (XXXVIII; 2.4 g; m.p. 143°–4° C.).

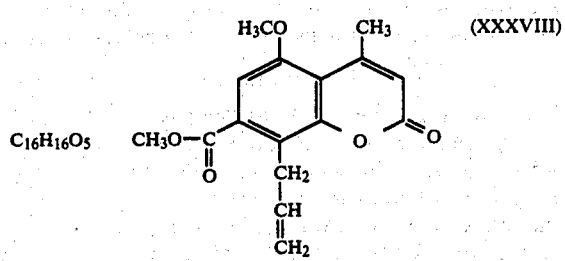

The 4-methyl-5-methoxy-7-acetoxy-8-allylcoumarin (XXXVIII; 2.5 g) was dissolved in AcOH (150 ml) and to this solution an acetic solution of bromine containing the stoichiometric amount of bromine was added with stirring. Stirring was continued for 20 min. after the addition was completed and then the solvent was evaporated off under reduced pressure. The residue by crystallization from MeOH gave 4-methyl-5-methoxy-7-acetoxy-8-(2',3'-dibromopropyl)coumarin (XXXIX; g 2.12; m.p. 184°–5° C.).

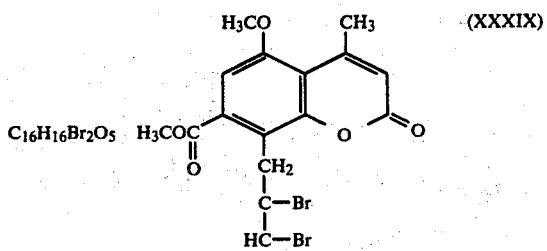

To an ethanolic solution (150 ml) of the 4-methyl-5-methoxy-7-acetoxy-8-(2',3'-dibromopropyl)coumarin (XXXIX) a 4% KOH ethanolic solution (35 ml) was added and the mixture refluxed for 1.5 h in the dark. After cooling the mixture was acidified with dil. HCl, the EtOH eliminated by evaporation at reduced pressure and the residue extracted several times with EtOAc. The residue obtained from the dried (Na$_2$SO$_4$) organic phase by evaporation of the solvent was purified via silica gel column chromatography by eluting with CHCl$_3$, giving 4,5'-dimethyl-5-methoxyangelicin (XL; 0.062 g; m.p. 226° C. (from MeOH).

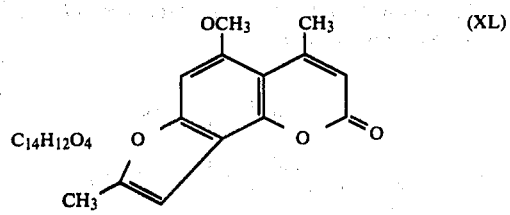

Water-soluble pharmaceutically acceptable salts of these compounds are conveniently obtained by O-demethylation of the 4,5'-dimethyl-5-methoxy-angelicin (XL) and insertion of N,N-dialkylaminoalkyl or aminoalkil groups.

EXAMPLE 28

Chloromethylation of the methylangelicins provides 4'-chloromethyl derivatives from which the hydroxymethyl, methoxymethyl and aminomethyl aminoalkoxymethyl and N,N-dialkylaminoalkoxymethyl derivatives are prepared. Thus to an AcOH solution (150 ml) of 4,5'-dimethylangelicin (XXVI; 3.0 g) chloromethylmethylether (23 ml) was added and the mixture allowed to react at room temperature for 15 h. Two further portions of chloromethylmethylether (10 ml) were added at 8 h intervals and after the last addition the mixture was allowed to react for over 36 h and kept overnight at 0° C. The precipitate so formed was collected crystallized from AcOH and provided 4,5'-dimethyl-4'-chloromethylangelicin ((XLI; 1.2 g; m.p. 213°–214° C.)

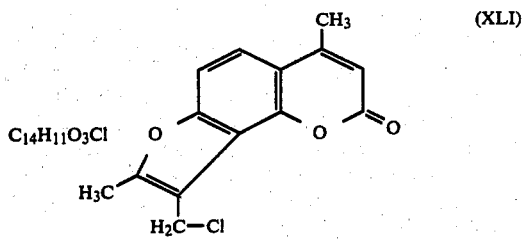

From the mother liquors after concentration and cooling at 0° C. a further crop of the product (1.5 g) was obtained. One-half gram of the product (XLI) was refluxed with water for 4 h; then the mixture was cooled and extracted with CHCl$_3$. The dried (Na$_2$SO$_4$) organic phase gave by evaporation of the solvent 4,5'-dimethyl-4'-hydroxy-methylangelicin (XLII; 0.37 g; m.p. 202° C. (from EtOAc)).

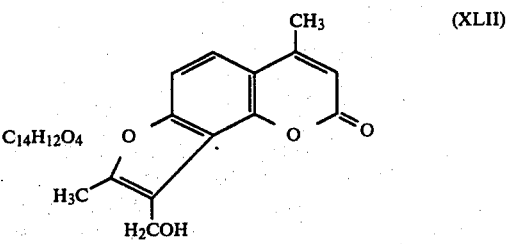

The 4,5'-dimethyl-4'-chloromethylangelicin (XLI; 0.5 g) was refluxed with acetic acid for 2 hours; then the mixture was cooled, diluted with water, neutralized by the addition of solid NaHCO$_3$ and extracted with CHCl$_3$. The dried (Na$_2$SO$_4$) organic phase gave by evaporation of the solvent 4,5′-dimethyl-4′-acetoxymethylangelicin (XLIII; 0.39 g; m.p. 109°–9° C. (from cycloexane/AcOEL)).

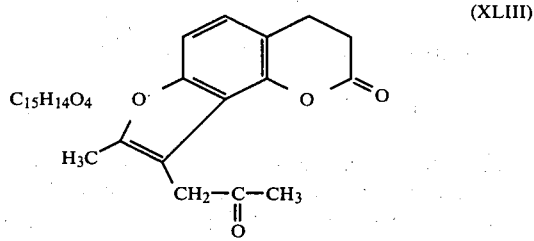

(XLIII)

The 4,5′-dimethyl-4′-chloromethylangelicin (XLI; 0.20 g) was refluxed with MeOH (75 ml) for 3 h, and after concentration down to a small volume the solution yielded 4,5′-dimethyl-4′-methoxymethylangelicin (XLIV; 0.14 g; m.p. 137° C. (from MeOH)).

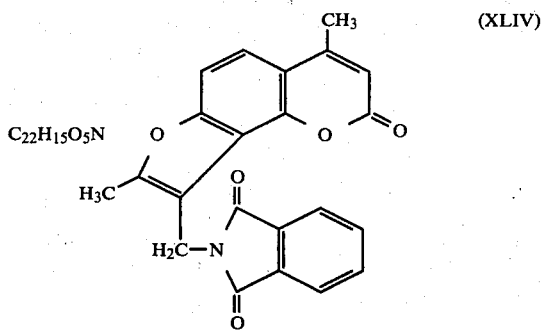

(XLIV)

4,5′-dimethyl-4′-chloromethylangelicin (XLI; 1.2 g), and potassium phtalimide (purified according to Gilman; 1.0 g) were suspended in N,N-dimethylformamide (120 ml) and the mixture was heated at 100° C. for 5 h; then the solvent was evaporated at reduced pressure. The residue was extracted with CHCl₃, the chloroformic extract washed three times with H₂O and dried (Na₂SO₄).

The solvent was evaporated and the organic layer yielded 4,5′-dimethyl-4′-phtalimidomethylangelicin (XLV; 0.9 g; m.p. 271°–5° C. (from CHCl₃/CCl₄ mixture)).

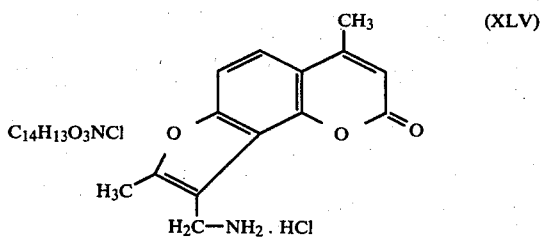

(XLV)

The 4,5′-dimethyl-4′-phtalimidomethylangelicin (XLV; 0.17 g) is suspended in 95% EtOH (25 ml) and to the suspension hydrazine hydrate (85% in H₂O; 0.3 ml) was added. The mixture was refluxed for 4 h and then a further addition of hydrazine hydrate (0.3 ml) was effected and the mixture refluxed again for 2 h. The solvent was evaporated and to the residue 0.1 M NaOH (70 ml) was added, then the alkaline solution was washed three times with portions of CHCl₃ (150 ml). The dried (Na₂SO₄) chloroformic solution was exhausted of solvent, the residue dissolved in 1.2 M HCl (40 ml) and the acidic solution washed several times with CHCl₃.

The aqueous phase was concentrated to dryness and the residue dissolved into dry EtOH; to this solution dry ether was added until thickened. After standing and cooling a crop of 4,5′-dimethyl-4′-aminomethylangelicin hydrochloride (XLVI; g 0.065; dec. 300° C.) was obtained, which is water soluble.

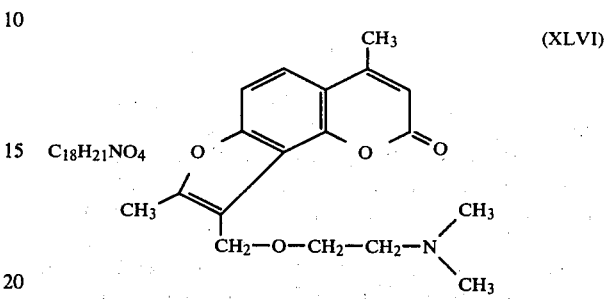

(XLVI)

Using the same procedure the analogous 4′-hydroxymethyl-, 4′-methoxymethyl- and 4′-aminomethyl-derivatives are also obtained from other aklylangelicins.

EXAMPLE 29

Finely subdivided silver (0.20 g) was dissolved in dimethylaminoethanol (10 ml) and to this mixture the 4,5′-dimethyl-4′-chloromethylangelicin (XLI; 0.50 g) dissolved in tetrahydrofuran (100 ml) was added; the mixture was allowed to react in the dark and at room temperature for 4 h, dil.HCl (200 ml) was then added and the mixture was extracted three times with portions of EtOAc (300 ml). The aqueous layer was neutralized by adding solid NaHCO₃ and extracted with EtOAc. From the dried (Na₂SO₄) organic layer the solvent and the dimethylaminoethanol excess were eliminated by evaporation under reduced pressure and the residue was purified by silica gel column chromatography and elution with MeOH. The 4,5′-dimethyl-4′-N,N-dimethylaminoethoxymethylangelicin (XLVII; g 0.075) was converted into the corresponding water soluble hydrochloride by dissolving it into a small volume of dil. HCl and then the water and HCl excess removed by vacuum evaporation.

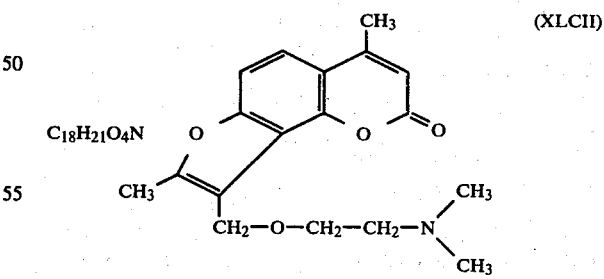

(XLCII)

In a similar manner other N,N-dialkylaminoalkoxymethyl- and aminoalkoxymethyl-derivatives are obtained.

DISCUSSION OF PHARMACOLOGICAL PROPERTIES OF THE ALKYLANGELICINS

The introduction of one or more alkyl groups, particularly methyl groups, in the angelicin molecule generally increases its capacity to form the dark complex, to photobind to DNA and consequently also its photobiological activity.

Dark complex formation: It is known from F. Dall-'Acqua, et al. Chem.-Biol. Interactions 21,103 (1978) that the intercalated complex formed by furocoumarins with DNA strongly affects the successive photoaddition increasing the rate of photobinding. Table II shows the binding parameters of the complexes formed between the alkylangelicins and DNA, that is K, the association constant of the complex referred to an isolated site, and 1/n, the frequency of the binding sites or number of molecules of angelicin bound for every nucleotide. These parameters have been determined according to the method of McChee and Von Hippel, J.Mol.Biol, 86, 469 (1974).

The introduction of one, two or three methyl groups causes a strong increase of the affinity towards DNA as shown by the strong increase of both the association constants and the increased number of binding sites.

gelicin significantly increases this affinity, that is K is increased more than 20 times.

This is due to the fact that, in addition to the intercalation, a second type of linkage takes place, specifically an ionic linkage between cationic head and a phosphate group of DNA, in the formation of the complex, thus increasing the affinity of these water soluble cationic compounds towards DNA.

Photobinding capacity to DNA: The introduction of one or two methyl groups in the molecule of angelicin leads to a strong increase of the photobinding to DNA; see Table II. Only in the case of 4,5,5'-trimethylangelicin, where three methyl groups have been introduced, does the photobinding capacity remain close to that of angelicin. Of the two water soluble cationic derivatives, while compound (XLVI) shows a photobinding capacity to DNA lower than that of angelicin, compound (XLVII) shows a strongly increased photobinding capacity. Table II also shows the rate constants values of

TABLE II

PHYSICO CHEMICAL PARAMETERS OF THE INTERACTION BETWEEN THE METHYLANGELICINS AND DNA IN VITRO BOTH in THE GROUND AND IN THE EXCITED STATE

| | | Binding parameters of the complexes with DNA (a) | | | |
|---|---|---|---|---|---|
| | | K | | 1/n | |
| | FUROCOUMARINS | (association constants) | relative (ang = 100) | frequency of binding sites | relative (ang = 100) |
| LINEAR AS | PSORALEN | 400 | 71.4 | 0.108 | 171 |
| REFERENCE | XANTHOTOXIN (8-MOP) | 740 | 132 | 0.128 | 203 |
| ANGULAR | 4'-N,N-dimethylaminoethoxymethyl-4,5'-dimethyl-angelicin | >10000 | >1700 | >0.15 | >230 |
| | 5-methylangelicin | 1560 | 278 | 0.071 | 112 |
| | 4'-hydroxymethyl-4,5'-dimethyl-angelicin | 1250 | 223 | 0.087 | 138 |
| | 4,5'-dimethylangelicin | 1410 | 252 | 0.094 | 149 |
| | 5,5'-dimethylangelicin | 1750 | 312 | 0.085 | 135 |
| | 5'-methylangelicin | 1200 | 214 | 0.073 | 116 |
| | 4'-methoxymethyl-4,5'-dimethyl-angelicin | 700 | 125 | 0.050 | 80 |
| | 4-methylangelicin | 1400 | 250 | 0.076 | 120 |
| | angelicin | 560 | 100 | 0.063 | 100 |
| | 4'-aminomethyl-4,5'-dimethyl-angelicin hydrochloride | 16300 | 2910 | 0.255 | 404 |

| | | Rate constants of the photo reactions with DNA (b) | | capacity to form inter-strand cross-linkages (psr = 100) |
|---|---|---|---|---|
| | FUROCOUMARINS | $K \times 10^{-2} \times min^{-1}$ | relative (ang = 100) | |
| LINEAR AS | PSORALEN | 3.8 | 345 | 100 (c) |
| REFERENCE | XANTHOTOXIN (8-MOP) | 2.3 | 209 | 63 (c) |
| ANGULAR | 4'-N,N-dimethylaminoethoxymethyl-4,5'-dimethyl-angelicin | ≃3.6 | ≃330 | 0 |
| | 5-methylangelicin | 3.41 | 298 | 0 |
| | 4'-hydroxymethyl-4,5'-dimethyl-angelicin | 3.2 | 2.81 | 0 |
| | 4,5'-dimethylangelicin | 4.0 | 363 | 0 |
| | 5,5'-dimethylangelicin | 2.73 | 248 | 0 |
| | 5'-methylangelicin | 2.11 | 191 | 0 |
| | 4'-methoxymethyl-4,5'-dimethyl-angelicin | 1.6 | 145 | 0 |
| | 4-methylangelicin | 1.61 | 146 | 0 |
| | angelicin | 1.1 | 100 | 0 |
| | 4'-aminomethyl-4,5'-dimethyl-angelicin hydrochloride | 0.8 | 72 | 0 |

(a) Determined according to Mc Ghee and Von Hippel, J. Mol. Biol., 86,469(1974).
(b) Determined according to F. Dall'Acqua, S. Marciani, F. Zambon and G. Rodighiero, Photochem. Photobiol., 29,489(1979).
(c) F. Dall'Acqua, S. Marciani, D. Vedaldi and G. Rodighiero, Z. Naturforsch., 29c,635(1974).

The introduction of a cationic moiety or head in addition to the two methyl groups to form, for instance, 4'-aminomethoxymethyl-4,5'-dimethylangelicin and 4'-N,N-dimethylaminoethoxymethyl-4,5'-dimethylanthe photoreactions determined according to Dall'Acqua et al. in Photochem. Photobiol., 29, 489 (1979).

All these compounds were not suitable to photoinduce in DNA inter-strand cross-linkages. In fact, DNA irradiated in their presence did not undergo any renaturation after heat denaturation and, moreover, its molecular weight, determined by sedimentation experiments, remained unmodified. These tests were carried out according to the method of F. Bordin et al., Photochem. Photobiol., 29,1063 (1979).

Photobiological activity: A significant test for assessing photobiological activity of alkylangelicins is the study of their capacity to inhibit DNA and RNA synthesis in Ehrlich ascites tumor cells. In Table III the capacity of inhibition is expressed as $ID_{50}$, that is the irradiation does, in terms of quanta at 365 nm, necessary to inhibit in these cells the 50% of the DNA and RNA synthesis in the presence of a constant amount of alkylangelicin. The alkylangelicins of the present invention generally show a strongly increased capacity to inhibit the DNA and RNA synthesis. Indeed only the water soluble cationic compound (XLVI) and compound (XXVII) show an activity lower than that of angelicin. Moreover, in general it can be observed that in this simple biological system a close correlation exists between photobiological activity and the capacity to induce photochemical lesions in DNA, that is photoreactivity.

Therapeutic indications: Therapeutic applications of the novel compounds herein disclosed relate to skin diseases that are characterized by hyperproliferation of the skin cells, such as psoriasis, mycosis fungoides and eczema, or by lack of skin pigmentation, such as vitiligo. The tendency of these compounds to realize in highly selective way photodamages to epidermal DNA causes the inhibition of the cell division with consequent normalization of the affected skin. The alkylangelicins according to the present invention can be therapeutically administered in two ways, that is by topical application and by oral administration plus UV-A irradiation.

Topical application of akylangelicins appears more simple and safe than the corresponding topical application of psoralens. The problems of skin-photosensitization present in the topical use of psoralens are absent with the novel compounds as is the lack of skin-phototoxicity. Moreover other side effects, such as the risk of hepatotoxicity and of cataract connected with the systemic use of psoralens, are also conveniently avoided by the topical application of alkylangelicins. Regarding the lower mutagenic activity, the risk of skin cancer seems to be markedly reduced in respect to psor-

TABLE III

PHOTOBIOLOGICAL PROPERTIES OF THE NEW METHYLANGELICINS

| | FUROCOUMARINS | Inhibition of DNA and RNA synthesis in Ehrlich ascite tumor cells (a) $ID_{50}$ (quanta × $10^{-18}$) ± S.E. | | | | Relative skin phototoxicity (b) (psr = 100) |
|---|---|---|---|---|---|---|
| | | DNA | relative (ang = 100) | RNA | relative (ang = 100) | |
| LINEAR AS REFERENCE | PSORALEN | 9.08 ±0.8 | 275 | 14 ± 1.1 | 166 | 100 |
| | XANTHOTOXIN (8-MOP) | 10.04 ± 0.6 | 249 | 25 ± 3.6 | 93 | 71 |
| | 4'-N,N-dimethylaminoethoxy-methyl-4,5'-dimethyl-angelicin | 8.6 ± 1.1 | 290 | 14.4 ± 2 | 162 | 0 |
| | 5-methylangelicin | 9.07 ± 1.2 | 275 | 8.3 ± 1.4 | 281 | 0 |
| | 4'-hydroxymethyl-4,5'-dimethyl angelicin | 9.2 ± 1.3 | 272 | 13.8 ± 1.8 | 169 | 0 |
| | 4,5'-dimethylangelicin | 10.87 ±1.54 | 230 | 13.5 ± 2.1 | 172 | 0 |
| | 5,5'-dimethylangelicin | 13.85 ± 1.2 | 180 | 6.56 ± 1.1 | 355 | 0 |
| | 5'-methylangelicin | 16.6 ± 1.4 | 150 | 17.4 ± 1.3 | 134 | 0 |
| | 4'-methoxymethyl-4,5'-dimethyl angelicin | 22.7 ± 2.5 | 110 | 13.8 ± 1.9 | 169 | 0 |
| | 4-methylangelicin | 24 ± 3.1 | 104 | 18.1 ± 1.7 | 129 | 0 |
| | angelicin | 25 ± 1.1 | 100 | 23.3 ± 1.6 | 100 | 0 |
| | 4'-aminomethyl-4,5'-dimethyl-angelicin hydrochloride | 100 | 25 | 100 | 23.3 | 0 |

(a) Determined according to Mc Ghee and Von Hippel, J. Mol. Biol., 86,469(1974).
(b) Determined according to F. Dall'Acqua, S. Marciani, F. Zambon and G. Rodighiero, Photochem. Photobiol., 29,489(1979).
(c) F. Dall'Acqua, S. Marciani, D. Vedaldi and G. Rodighiero, Z. Naturforsch., 29c,635(1974).

Mutagenic activity: The mutagenic activity of 4,5'-dimethylangelicin has been studied on two *E. coli* strains 2P2 trp−; WP2 trp−uvrA−. As reference compounds two linear furocoumarins, psoralen and 8-methylpsoralen, have also been tested under the same conditions. See S. Venturini, et al Comparative Mutagenitity of Linear And Angular Furocoumarins in *E. coli* Strains Deficient In Known Repair Functions; supra.

The mutation frequency observed in the wild type is very high with the two linear furocoumarins while it is of no appreciable level with 4,5'-dimethylangelicin. Its mutagenic activity becomes detectable only in the uvrA− strain, deficient in the DNA repair functions. The mutagenic activity of 5-methylangelicin, tested in *Salmonella typhimurium* TA 100 his G46 (missense mutation) (uvrB− rfa) pKM101 (Ames test), resulted of the same order of magnitude as that of 4,5'-dimethylangelicin.

alens.

Before performing clinical experiments directly on humans to evaluate the therapeutical effectiveness of the alkylangelicins according to the present invention, preliminary experiments were carried out on laboratory animals.

In fact, the evaluation of the extent of inhibition of the synthesis of the epidermal DNA on the skin of mice "in vivo" after topical application of the compounds and UV-A irradiation, gives precise information on the possible therapeutical effectiveness of the compounds on humans—in spite of the fact it is impossible to indue psoriasis and similar skin diseases in laboratory animals.

Table IV presents the inhibition data.

To obtain these data the drugs were applied on depilated skin of abdomen of female mice using 0.01% methanol solutions (50 g/cm$^2$). After keeping the mice in a dark room for 45 min., the abdomens were irradiated with UV-A light (9 J/cm$^2$) and then $^3$H-thymidine (70

Ci/mM; 10 Ci) was injected i.p. Thirty minutes later the mice were sacrificed, the irradiated skins removed and the epidermis isolated according to the method of T. J. Slaga, et al Cancer Res., 33,769–776 (1973), homogenized by using a Vortex mixer and subjected to DNA extraction according to E. Szybalska et al. DNA samples were dissolved in water and their specific radioactivity determined.

TABLE IV

Inhibition of epidermal DNA synthesis in the mouse "in vivo" after topical application of angelicin derivatives and UV-A irradiation.

| | Percent inhibition ± standard error |
|---|---|
| No drug, solvent alone | 2.5 ± 1.3 |
| psoralen | 47.8 ± 7.9 |
| 8-methoxypsoralen (8-MOP) | 61 ± 1.6 |
| 4,5'-dimethylangelicin | 37.6 ± 4.9 |
| 5-methylangelicin | 47.5 ± 1.19 |
| 5,5'-dimethylangelicin | 48.3 ± 2.9 |
| 4,5-dimethylangelicin | 36 ± 1.1 |
| 4-methylangelicin | 68.5 ± 19.5 |
| 4'-dimethylaminoethoxymethyl-4,5'-dimethylangelicin | 29.4 ± 16.2 |
| 4'-acetoxymethyl-4,5'-dimethylangelicin | 10.6 ± 4.5 |
| angelicin | 17.5 ± 2.5 |

Proc. Natl. Acad. Sci. U.S., 48, 2026–2034 (1962). DNA samples were dissolved in water and their specific radioactivity determined.

The percent inhibition of DNA synthesis observed in each sample was calculated assuming as a control the radioactivity incorporation observed in epidermal DNA of the back skin of the same animal, processed in the same manner. The specific activities observed in the control skin were in the range of $0.9–1.2 \times 10^4$ dpm/mg DNA.

Each drug substance was studied using at least six mice.

The data of Table IV evidence that the alkylangelicins of the present invention demonstrate a substantial capacity to inhibit the synthesis of mice epidermal DNA. These date show a correlation with the clinical data demonstrating that such a test gives significant information of the possible therapeutic effectiveness of this class of compounds in humans therapy.

Clinical data: The effectiveness of certain representative alkylangelicins according to the present invention, specifically 5-methylangelicin, 4,5'-dimethylangelicin, 4'-hydroxymethyl-4,5'-dimethylangelicin, 4'-hydroxymethyl-4,5'-dimethylangelicin and 4,5-dimethylangelicin, has been tested by measuring their capacity to resolve psoriasis in various patients. For a direct comparison the efficacy of the parent unsubstituted angelicin and that of three very effective linear furocoumarins, that is 8-methoxypsoralen (8-MOP), 5-methoxypsoralen (5-MOP), and 4,5',8-trimethylpsoralen (TMP) were also tested.

In each treatment four areas of the affected skin were used;

(a) In the first area an alcohol lotion, containing 10% glycerine, of the tested compound (0.1% w/v) was applied until a concentration of 20 g/cm² was reached then left to evaporate by the heat of the body. After half an hour the area was irradiated with high intensity UV-A emitting low pressure mercury fluorescent lamps with a wavelength of 320–400 nm. The irradiation doses were selected in the range of 4.5–13 J/cm² for each application as a function of the sensitivity of the skin of the patients; when the skin sensitivity was higher, the light doses were lower and vice versa.

(b) A second area was treated with an alcohol solution of the drug as in (a) but it was covered and maintained in the dark.

(c) A third area, where the drug was not applied, was irradiated as in (a) but in general with higher UV-A doses.

(d) A fourth area was not treated at all, neither with the drug, not with UV-A.

The treatment with the alkylangenlicins referred to above was repeated 5 time a week for two or more weeks; the total number of treatments was between 8 and 20 per subject. In some cases, as for instance with 5-methylangelicin, a good clearing of psoriasis was observed after 8 treatments.

In order to avoid induction of photosensitization processes such as redness and erythema in the reference tests made with the linear furocoumarins 8-MOP, 5-MOP, TMP, lower light doses were used than in the case of alkylangelicins, the treatments were repeated at a frequency of no more than three times a week.

A summary of the clinical data obtained in this manner is shown below in Table V. The decreasing order of efficacy is the following: 5-methylangelicin, 4,5'-dimethylangelicin, 4'-hydroxymethyl-4,5'-dimethylangelicin, 4,5-dimethylangelicin, the last-mentioned compound being equal to angelicin. 5-methylangelicin appears very active, probably more active than the same amount of 8-MOP. In addition to a very high efficacy 5-methylangelicin allows clearing of the psoriasis to be accomplished more rapidly than 8-MOP because the treatments can be repeated at a greater frequency, for example one treatment every day for 5 days a week, owing to the absence of skin phototoxicity. The UV-A light alone, as indicated, causes only very slight effects, but at much higher light doses. No effect can be observed in the skin treated with the drug and maintained in the dark.

As with the psoralens so to may the alkylangelicins of the present invention be administered orally. In fact, their acute toxicity in mice is of the same order of magnitude as that of psoralens, that is $LD_{50}$ of 8-MOP = 0.8 g/Kg; $LD_{50}$ of 5-methylangelicin 2 g/Kg and $LD_{50}$ of 4,5'-dimethylangelicin 2.5 g/Kg.

TABLE V

Results of topical photochemotherapy with alkylangelicin in patients

| | Furocoumarin | No. of patients Listed | Excellent | Good | Fair | Poor |
|---|---|---|---|---|---|---|
| (1) | 8-methoxypsoralen* (8-MOP) | 10 | 3 | 3 | 2 | 2 |
| (2) | 5-methoxypsoralen* (5-MOP) | 9 | 0 | 4 | 1 | 4 |
| (3) | 4,5',8-trimethyl psoralen* (TMP) | 8 | 2 | 2 | 2 | 2 |
| (4) | Angelicin* | 8 | 0 | 0 | 0 | 8 |
| (5) | 4,5'-dimethyl-angelicin | 4 | 0 | 1 | 3 | 0 |
| (6) | 4'-hydroxymethyl-4,5'-dimethylan gelicin | 4 | 0 | 1 | 2 | 1 |
| (7) | 5-methylangelicin | 7 | 2 | 5 | 0 | 0 |
| (8) | 4,5-dimethylange-licin | 2 | 0 | 0 | 0 | 2 |
| (9) | UV-A only | 17 | 0 | 1 | 1 | 15 |
| (10) | CONTROL (drug without treatment | | | | | |

TABLE V-continued

| Furocoumarin | Results of topical photochemotherapy with alkylangelicin in patients | | | | |
|---|---|---|---|---|---|
| | No. of patients Listed | Excellent | Good | Fair | Poor |
| with light) | 17 | 0 | 0 | 0 | 17 |

Results of Compounds = 1, 2 and 3 are based on 10–12 therapies only, while the results of Compounds = 4, 5, 6, 7 and 8 are based on 10–18 therapies: Excellent = 90% clearance; Good = 70–90%; Fair = 50–70%; Poor 40%.
*8-MOP, 5-MOP - TMP and angelicin are included as reference compounds Upon oral administration the alkylangelicins according to our invention behave in a way similar to psoralens; they exhibit in fact evident tropism for the skin as shown by tests carried out on mice. Due to the localization of the drug at the level of the skin, when the latter is irradiated with UV-A, a photoreaction between the drug and the epidermal DNA occurs. The photodamages deriving from this photoreaction cause the inhibition of the cell division, in a similar manner as it occurs with the psoralens. There is, however, a rather fundamental difference between the effect of psoralens and angelicins. The angelicins in fact, induce only monofunctional lesions to the DNA, whereas psoralens induce both mono- and bifunctional lesions. Mono- and bifunctional lesions cause more pronounced biological consequences such as higher mutation frequency, higher risk of skin cancer and skin-phototoxicity.

Considering that the topical skin tests carried out on mice to evaluate the effectiveness of these substances has yielded data which correlate well with the clinical data, such a test conveniently modified has been adopted to evaluate the effectiveness of the alkylangelicins after oral administration followed by UV-A irradiation.

In this connection experiments have been conducted using mice 20±2 g in weight, that were starved for three hours before oral administration of the alkylangelicins. Groups of 5 mice were fed a suspension of 0.5% methylcellulose in water containing the alkylangelicins of the invention at a dosage of 0.25 g/Kg. The animals were kept in the dark for two hours, that is for the time necessary for absorption, systemic distribution and localization of the drug at the level of the skin. The animals were then irradiated with UV-A light, 9 J/cm². Later the animals were sacrificed and the inhibition of the epidermal DNA synthesis was tested; the results obtained are reported in Table VI. The skin on the back, protected from light by a dark paper, was assumed as a control. As a reference 8-MOP, used under the same experimental conditions, was also tested. The significant activity of the alkylangelicins according to the present invention, higher than that of 8-MOP, in inhibiting the epidermal DNA synthesis in mice upon oral administration allows one to consider these compounds as also being effective for oral administration to humans for photochemotherapy of psoriasis and of other skin diseases that are characterized by cellular hyperproliferation.

TABLE VI

Inhibition of the synthesis of epidermal DNA of the mouse in vivo after oral administration of angelicin derivatives and UV-A irradiation of the skin (8-MOP is reported as reference compound).

| | Percent inhibition ± standard error |
|---|---|
| No drug | 3.2 ± 1.8 |
| 8-methoxypsoralen (8-MOP) | 39.1 ± 3.7 |
| 4,5'-dimethylangelicin | 51.0 ± 8.0 |
| 4,5-dimethylangelicin | 55.0 ± 6.0 |
| 4'-hydroxymethyl-4,5'-dimethylangelicin | 54.2 ± 6.8 |
| 4'-acetoxymethyl-4,5'-dimethylangelicin | 64.8 ± 13.9 |
| angelicin | 28 ± 2 |

For oral administration to humans for photochemotherapy of psoriasis and of other skin diseases that are characterized by cellular hyperproliferation. Formulations and pharmaceutical compositions- The following pharmaceutical compositions may be used for oral administration of the alkylangelicins:

| Capsules | |
|---|---|
| Alkylangelicin (drug) | 30 mg |
| Lactose (diluent) | 70 to 120 mg |
| Mg stearate (lubricant) | 1 to 1.5 mg |
| Na Lauril sulphate (wetting) | 1.5 mg |
| included in an appropriate gelatin capsule. | |
| Tablets | |
| Alkylangelicin (drug) | 30 mg |
| Lactose (diluent) | 240 mg |
| Mg stearate (lubricant) | 2 mg |
| Maize starch (disintegrant and lubricant) | 60 mg |
| Microcrystalline cellulose (lubricant and disintegrant) | 10 mg |
| Polyvinylpyrrolidone (binder) | 3% |
| Na Lauril sulphate (wetting) | 3 mg |

One or more of the above-described tablets or capsules may be administered orally about two hours before irradiation. The exact dosage is of course dependent upon the bodyweight, age and sex of the patient.

What is claimed is:

1. A compound for the photochemotherapy of psoriasis and related skin diseases characterized by cellular hyperproliferation, said compound having the formula:

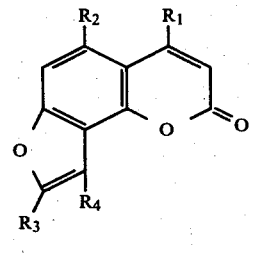

in which
$R_1$ and $R_3$, which may be the same or different, are hydrogen, methyl or ethyl;
$R_2$ is hydrogen, methyl or ethyl, and
$R_4$ is methoxymethyl, hydroxymethyl, acetoxymethyl or a group of the formula:

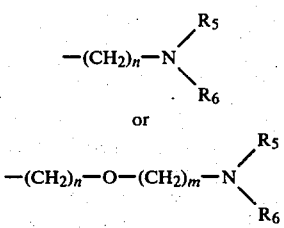

wherein $R_5$ and $R_6$ are independently hydrogen, methyl or ethyl and n and m are independently an integer of 1 to 3, or a pharmaceutical salt thereof.

2. A furocoumarin selected from the group consisting of:
   4,5'-dimethyl-4'-hydroxymethylangelicin,
   4,5'-dimethyl-4'-(N,N-diethyl)aminoethoxymethylangelicin,
   4'-acetoxymethyl-4,5'-dimethyl-4,5'-dimethylangelicin,
   4'-N,N-dimethylethoxymethyl-4,5'-dimethylangelicin
or a pharmaceutically acceptable salt thereof.

3. A pharmaceutical composition for topical application for the photochemotherapy of psoriasis containing a therapeutically effective amount of a compound of claim 1 or 2 together with an acceptable topical carrier or diluent.

4. The pharmaceutical composition of claim 3 wherein said compound is present in an amount of from about 0.05 to about 0.4% w/v.

5. A pharmaceutical composition for the photochemotherapy of psoriasis containing a therapeutically effective amount of a compound of claim 1 or 2 together with a pharmaceutically acceptable carrier or diluent.

6. The pharmaceutical composition of claim 5 wherein about 30 mg said compound is present and the composition is a tablet or capsule for oral administration.

7. A photochemotherapeutic method of treating psoriasis or skin disease sensitive to such treatment comprising (a) administering to a person suffering therefrom an effective amount of a compound of the formula:

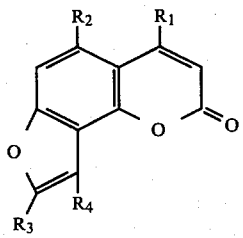

in which
  $R_1$ and $R_3$, which may be the same or different, are hydrogen, methyl or ethyl;
  $R_2$ is hydrogen, methyl, ethyl, methoxy or a group of the formula

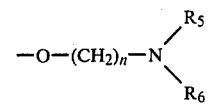

and $R_4$ is hydrogen, methyl, ethyl, methoxymethyl, hydroxymethyl, acetoxymethyl or a group of the formula:

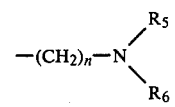

or

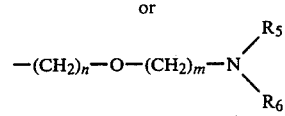

wherein $R_5$ and $R_6$ are independently hydrogen, methyl or ethyl and n and m are independently an integer of 1 to 3, or a pharmaceutical salt thereof, and thereafter (b) irradiating the affected skin area with UV-A light for a period of time sufficient to provide an irradiation dose of about 3 to about 20 $J/cm^2$, and (c) repeating steps (a) and then (b) until the psoriasis or skin disease symptoms are ameolerated.

8. The method of claim 7 wherein the compound is administered in step (a) is applied directly to the affected skin area in the form of a topically applied pharmaceutical composition and the topically applied pharmaceutical composition remains in contact with the skin during step (b).

9. The method of claim 8 wherein the topically applied pharmaceutical composition is applied in step (a) and irradiated in step (b) from about 3 to about 5 times per week for a period of at least two weeks.

10. The method of claim 7 wherein the compound in step (a) is administered orally and the time period between step (a) and the irradiation step (b) is between about 2 to 3 hours until the orally administered compound is localized at the site of psoriasis or skin disease.

11. The method of claim 7, 8, 9 or 10 wheein the compound is:
   5-methylangelicin,
   4,5'-dimethylangelicin,
   4'-hydroxymethyl-4,5'-dimethylangelicin or
   4,5-dimethylangelicin.

* * * * *